(12) United States Patent
Nissen et al.

(10) Patent No.: US 9,501,820 B2
(45) Date of Patent: Nov. 22, 2016

(54) AUTOMATED NITAL ETCH INSPECTION SYSTEM

(71) Applicant: BELL HELICOPTER TEXTRON INC., Fort Worth, TX (US)

(72) Inventors: Jeffrey P. Nissen, Fort Worth, TX (US); Edward Hohman, Arlington, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 228 days.

(21) Appl. No.: 14/147,195

(22) Filed: Jan. 3, 2014

(65) Prior Publication Data
US 2015/0193919 A1 Jul. 9, 2015

(51) Int. Cl.
| | |
|---|---|
| G06T 7/40 | (2006.01) |
| G06T 7/00 | (2006.01) |
| G01M 13/02 | (2006.01) |
| G01N 21/88 | (2006.01) |
| G06K 9/32 | (2006.01) |
| H04N 7/18 | (2006.01) |
| H04N 5/225 | (2006.01) |
| G01N 21/91 | (2006.01) |
| G01N 21/95 | (2006.01) |
| H04N 101/00 | (2006.01) |

(52) U.S. Cl.
CPC .......... *G06T 7/0004* (2013.01); *G01M 13/021* (2013.01); *G01N 21/8803* (2013.01); *G01N 21/91* (2013.01); *G01N 21/95* (2013.01); *G06K 9/3233* (2013.01); *G06T 7/001* (2013.01); *H04N 5/2256* (2013.01); *H04N 5/2257* (2013.01); *H04N 7/185* (2013.01); *G06K 2207/1012* (2013.01); *G06T 2207/10004* (2013.01); *G06T 2207/10052* (2013.01); *G06T 2207/30116* (2013.01); *G06T 2207/30168* (2013.01); *H04N 2101/00* (2013.01)

(58) Field of Classification Search
CPC .................. B81C 1/00539; B81C 2201/0133
See application file for complete search history.

(56) References Cited

U.S. PATENT DOCUMENTS 5,732,147 A * 3/1998 Tao ...................... B07C 5/3422
348/89
6,064,429 A 5/2000 Belk
(Continued)

FOREIGN PATENT DOCUMENTS

| EP | 2363575 A2 | 2/2011 |
| JP | 2003075361 A | 3/2003 |
| WO | 2012122542 A2 | 9/2012 |

OTHER PUBLICATIONS

Domke W., "Metallographische Prufung", Werkstoffkunde Und Werkstoffprufung, Jan. 1, 1981, pp. 358-371, Girardet Buchverlag, DE, ISBN: 3-7736-1219-2. Search Report dated Apr. 14, 2014 from counterpart EP App. No. 14152499.1.
(Continued)

*Primary Examiner* — Christopher Findley
(74) *Attorney, Agent, or Firm* — James E. Walton

(57) ABSTRACT

A system and method to inspect flaws associated with a part. The system includes a first image capturing device configured to capture a first set of images of the part and a computer operably associated with first image capturing device and configured to receive and analyze the first set of images. The method includes treating the part with a nital etchant solution, capturing a first set of images of an outer surface of the part with the first image capturing device, and identifying a part defect with an algorithm associated with the computer.

18 Claims, 4 Drawing Sheets

(56) References Cited

U.S. PATENT DOCUMENTS

| | | | | |
|---|---|---|---|---|
| 2001/0043736 A1* | 11/2001 | Nakajima | ............ | G06T 7/0002 382/152 |
| 2002/0154811 A1* | 10/2002 | Katsuta | ................. | G01N 21/91 382/151 |
| 2011/0136408 A1* | 6/2011 | Frazee | ................ | B23F 23/1218 451/8 |
| 2013/0176402 A1* | 7/2013 | Young | .................... | G02B 21/22 348/47 |

OTHER PUBLICATIONS

Office Action dated May 9, 2014 from counterpart EP App. No. 14152499.1.
Summons to attend Oral Proceedings dated Mar. 6, 2015 from counterpart EP App. No. 14152499.1.
Wikipedia, "METALLOGRAFIE," Dec. 3, 2014, pp. 1-7, XP007923003, Retrieved from the Internet: URL: http://de.wikipedia.org/w/index.php?title=Metallografie&pri, retrieved on Jun. 15, 2015.

* cited by examiner

AUTOMATED NITAL ETCH INSPECTION SYSTEM

BACKGROUND

1. Field of the Invention

The present application relates generally to quality control inspections, and more specifically, to an automated quality control inspection system utilizing nital etch processing.

2. Description of Related Art

Newly manufactured parts, such as gears, are required to pass a quality control inspection prior to use. Conventional inspections include the initial step of undergoing a pretreatment process that visually enhances defects present with the gear. In one known process, the gear is pretreated with an etching solution, such as a mixture of alcohol and nitric acid, which in turn provides a visual indication of flaws.

FIG. 1 is a simple schematic of an inspector 101 performing a visual inspection of a gear 103 that has been pretreated with the etching solution. The inspection process, while effective under controlled conditions, can be affected, for example, by inspector fatigue, inspector-to-inspector variability, and so forth, all of which could result in poor inspection reliability and in some cases, result in catastrophic failure of the gear during use. The inspection process can also be time-consuming; an undesired feature when inspecting a large number of gears.

Although the foregoing developments in quality control inspection represent great strides, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
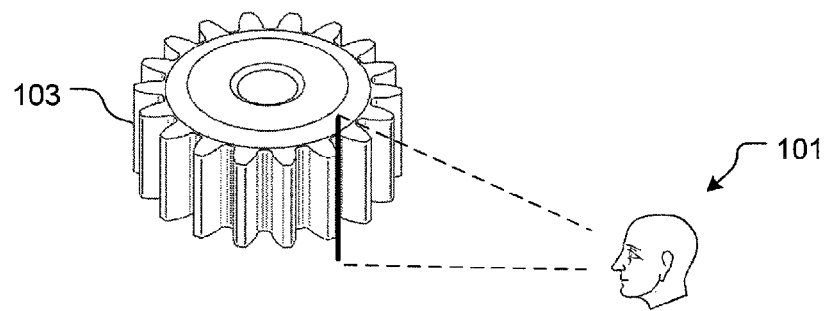
FIG. 1 is a simple schematic of a conventional quality control inspection process.

While the system and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the apparatus and method are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system of the present application overcomes the above-listed problems commonly associated with conventional quality control inspections. Specifically, the system is automated and is provided with one or more image capturing devices configured to capture the entire surface area of the gear and configured to relay the captured images to a computer for analysis. The computer includes the necessary software, hardware, and algorithms to analyze the set of captured images for determining if flaws in the gear exist. The system provides significant advantages, namely, the system is automated, thereby creating consistency in the quality control inspection process, provides an archive of the inspection result, and the system provides a more rapid approach to inspecting a larger quantity of gears in a shorter duration of time, which in turn greatly reduces the time and costs associated with the quality control inspection process. Further detailed description of these features are provided below and illustrated in the accompanying drawings.

The system and method of the present application will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Figure 2:
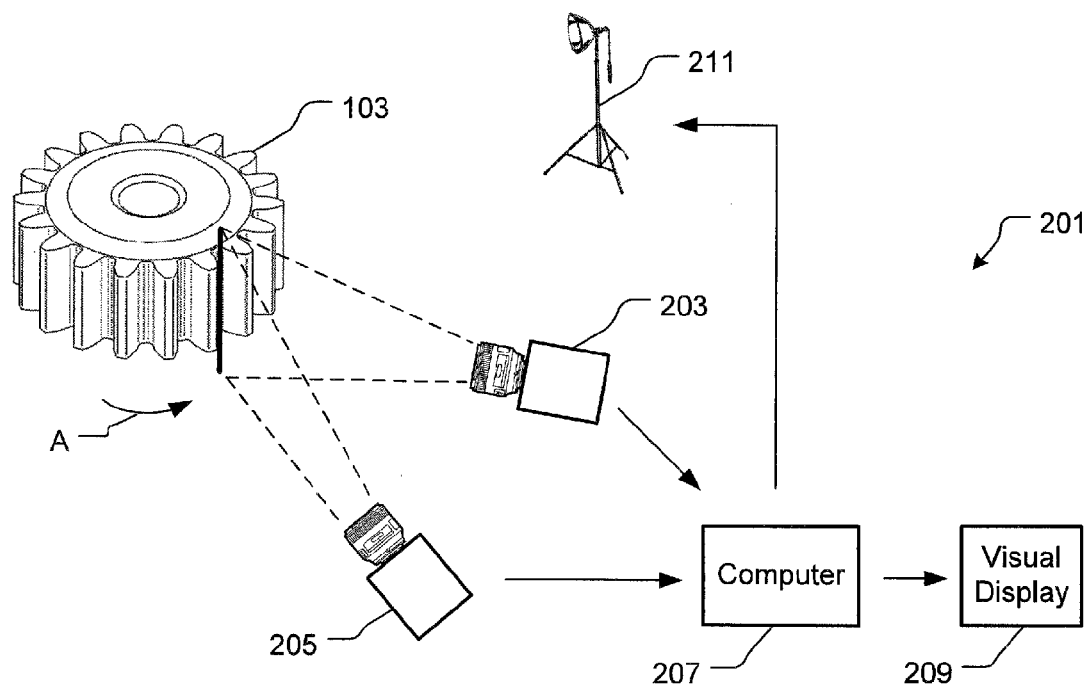
FIG. 2 is an oblique view of a quality control inspection system in accordance with a preferred embodiment of the present application.

Referring now to the drawings wherein like reference characters identify corresponding or similar elements throughout the several views, FIG. 2 depicts a quality control inspection system 201 in accordance with a preferred embodiment of the present application. System 201 is an automated system configured to rapid inspect a large number of gears in a short duration. In one embodiment, the system is mobile, thereby allowing inspection in situ while the part remains assembled. In the contemplated embodiment, system 201 includes one or more image capturing devices 203, 205, e.g., high resolution cameras, operably associated with a computer 207.

During use, the image capturing devices 203, 205 are configured to capture a set of images at one or more angles relative to the gear and configured to relay the set of captured images to computer 207. In the preferred embodiment, image devices 203, 205 capture the entire surface area of gear 103, thereby allowing computer 207 to analyze the entire surface structure of gear 103 for defects. Image capturing devices 203, 205 are preferably high resolution cameras in the contemplated embodiment; however, laser based, alternating electric current, infrared imaging devices, and/or other suitable types of image capturing devices could also be used in lieu of the preferred embodiment.

Computer 207 is provided with the necessary hardware, software, and algorithms to analyze the set of captured images and to thereafter determine whether flaws in the gear exist. A display 209 operably associated with computer 207 is utilized to provide visual inspection to an inspector. System 201 is further provided with one or more lighting systems 211 that can be controlled via computer 207. The lighting system is configured to provide light consistency during inspection of the large quantity of gears.

It will be appreciated that system 201 is configured to provide rapid means to inspect a plurality of gears in a short duration of time, which in turn results in reduced time exhausted during the inspection process, increased consistency, and considerable savings.

Although system 201 is shown associated with quality control of gears, it should be understood that the features discussed herein could also be incorporated with a quality control system that inspects other types of parts requiring visual inspection and should not be limited solely to gears.

Figure 3:
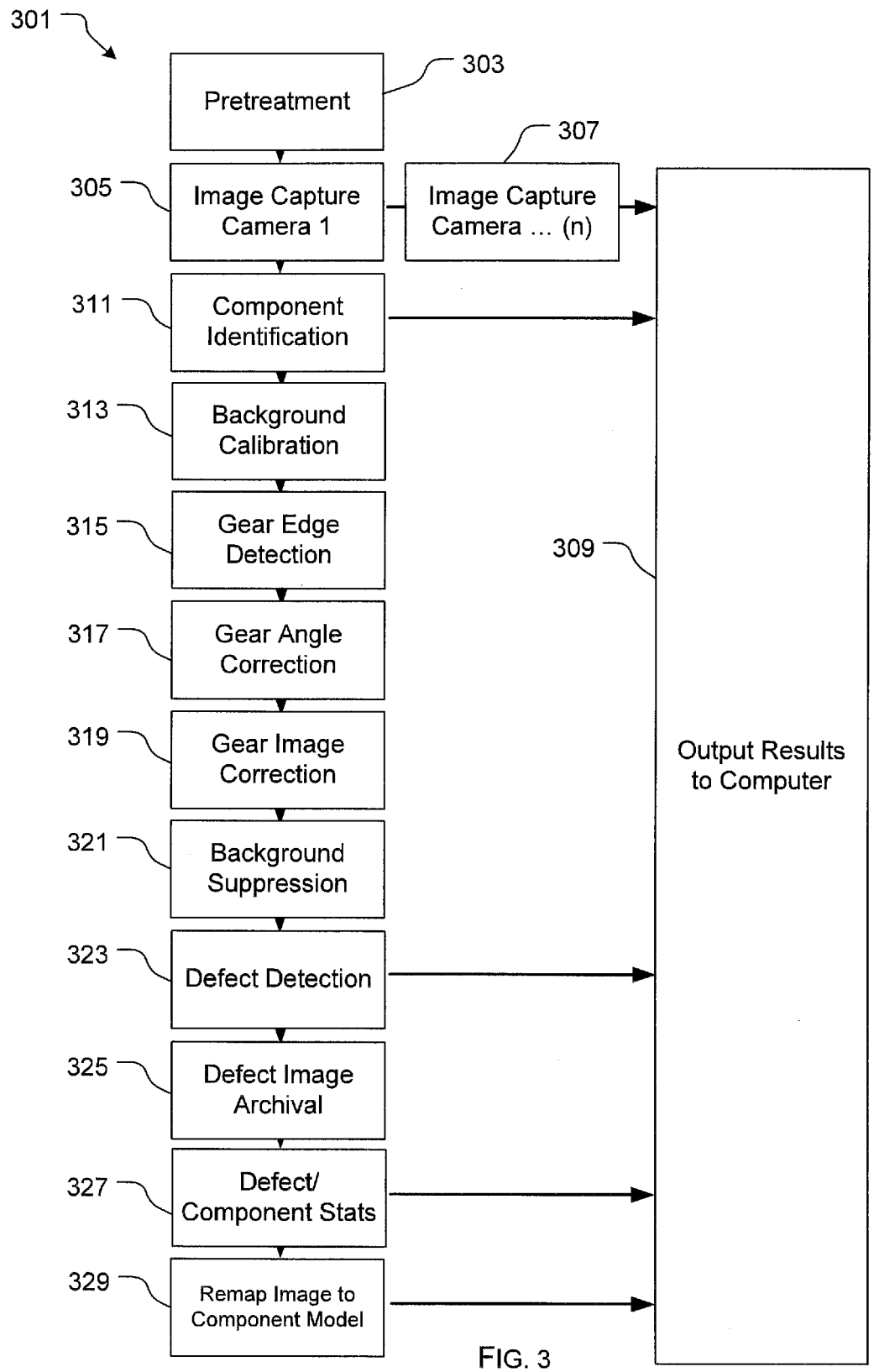
FIG. 3 is a flowchart depicting the inspection process in accordance with a preferred method of the present application.

FIG. 3 shows the preferred method, as depicted in a flowchart 301. The contemplated method includes the process of treating the gear 103 prior to inspection, as indicated by step 303. The pretreatment process includes, for example, a nital etch treatment, wherein the gear is treated within a nital etching solution, which in turn provides visual indication of defects in the material, e.g., over-temper, under-temper, surface structural deficiencies, material discoloration, and the like.

After the pretreatment process, the gear is secured to a structure, preferably a rotating structure, as indicated by rotating arrow "A," that allows image capturing of the entire gear surface area during the rotation process. While secured to the structure, one or more the image capturing devices, e.g., a high-resolution camera, captures the surface area of the gear, as indicated by steps 305, 307. It will be appreciated that multiple image capturing devices and robotic positioning could be utilized to increase the efficiency of detecting defections. The next step includes relaying the captured images to the computer 309 for processing.

Step 311 includes the process of determining the type of part being inspected. It will be appreciated that a plurality of different types of gears, along with other parts, are inspected by the contemplated quality control system. As such, the computer is configured to first recognize the type of part being inspected. This feature can be achieved either autonomously by a computer storage database or manually by the inspector input.

Step 313 includes the process of capturing a background image, which is later suppressed from the set of captured images, as shown in step 323.

Steps 315, 317, and 319 include the processes of preparing the set of captured images for analysis. Specifically, step 315 includes the step of determining the gear edge, which is later used to correct the angle orientation and image of the gear, as indicated by steps 315, 317. It should be noted that it is generally common to capture images at an offset angle, especially when a plurality of cameras are utilized. For this reason, the angle of the captured images is aligned prior to analysis Step 323 includes the process of analyzing the captured image. In one contemplated embodiment, the set of images can be compared with the same type of part devoid of flaws. Any discrepancy between the compared parts could be picked up by the computer, which in turn would either autonomously reject the part and/or notify the inspector of the flaws via the display. It is also contemplated utilizing other methods to determine flaws, for example, the computer could be configured to include the process of simply identifying discolorations in the material, gear dimensional characteristics, and the like, which in turn causes the computer to reject the part.

As depicted in step 325, the preferred method also includes archiving the defective parts, which data is then used to determine statistics for quality feedback, as indicated by step 327. Finally, the last step includes the process of remapping the image to the component mode, as indicated by step 329.

Figure 4:
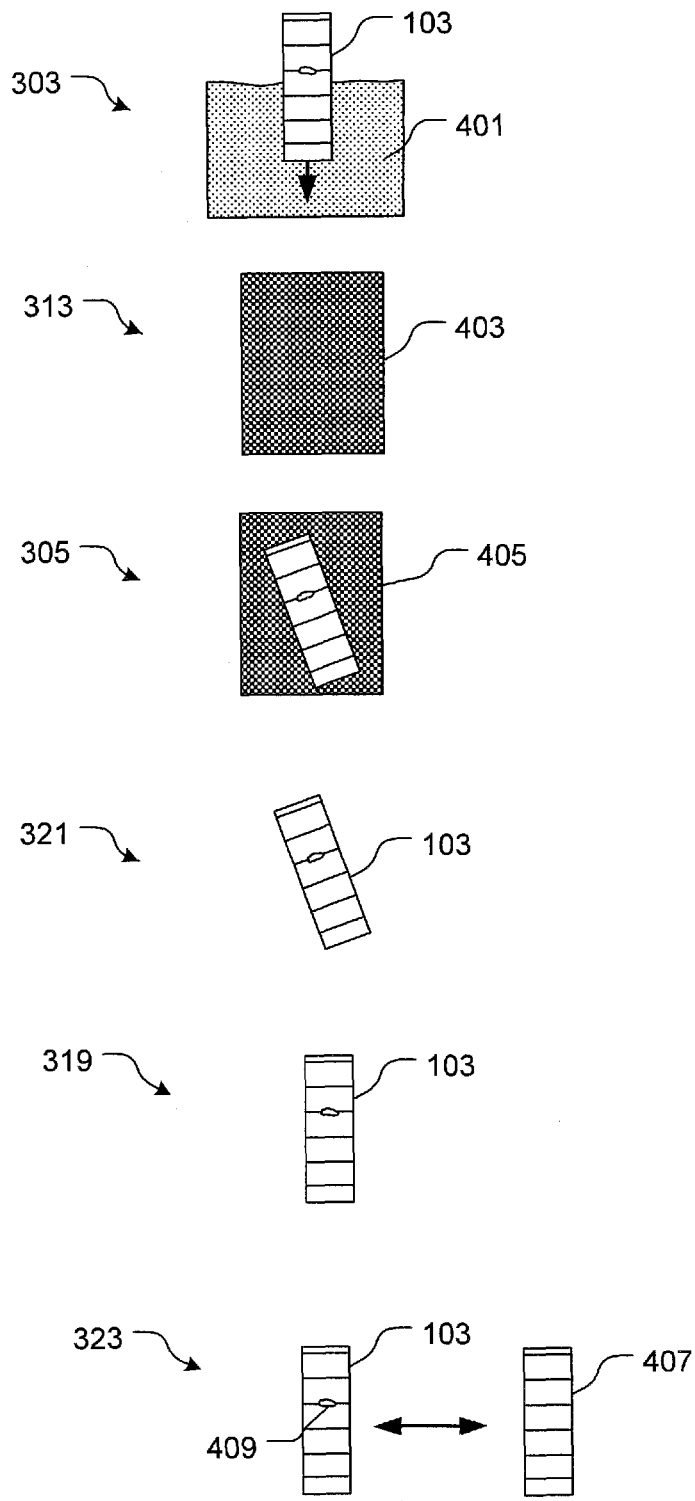
FIG. 4 is a schematic view of the method of FIG. 3.

The process steps are further discussed and shown in FIG. 4. As depicted, gear 103 is treated with a solution 401 that visually enhances the defects, for example, nital etchant. An image background 403 is taken, as discussed in step 313, which is later suppressed, as discussed in step 321.

The gear 103 is mounted to a structure (not shown) and one or more image capturing devices capture an image 405 of the gear along with the background. After suppressing the background image, the computer detects the gear edge and corrects angle orientation of the captured gear image for comparison with an image of the same type of gear 407 devoid of defects. Comparison with gear 407 allows the computer to determine whether a defect 409 is present on the gear. As discussed above, another embodiment could include the process of detecting discolorations and the like present on the set of captured images.

Figure 5:
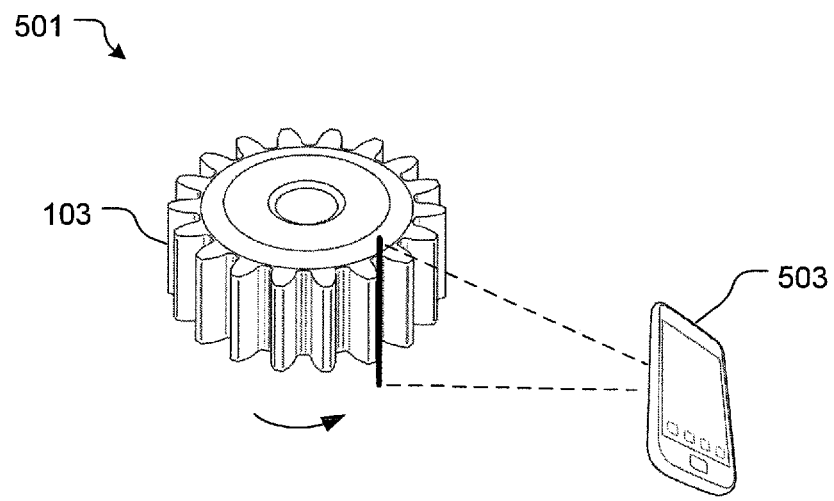
FIG. 5 is an oblique view of a quality control inspection system in accordance with an alternative embodiment of the present application.

Referring now to FIG. 5 in the drawings, a system 501 is shown in accordance with an alternative embodiment of the present application. System 501 is substantially similar in function to system 201 and includes one or more of the features discussed above. However, system 501 is configured to be mobile, thus allowing inspection in situ, wherein the part, e.g., gear 103 can remain assembled to the one or more operably associated structures during the inspection process. For example, gear 103 associated with a transmission of an aircraft can be inspected for defects caused by wear and tear with a mobile device 503, such as a smartphone, having an image capturing device associated therewith. This feature provides significant advantages, namely, the gear 103 can be inspected without the time-consuming process of disassembly and assembling the gear on a structure for inspection.

It is apparent that a system and method with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A quality control inspection system, comprising:
   a first image capturing device configured to capture a first set of images of a part from a first angle relative to the part;
   a second image capturing device configured to capture a second set of images of the part from a second angle relative to the part, the second angle being different from the first angle; and a computer operably associated with the first image capturing device and the second image capturing device, the computer being configured to receive and analyze the first set of images and the second set of images and configured to identify a part flaw, the computer having an image of a second part devoid of flaws;

wherein the first and second image capturing devices are repositionable relative to each other such that the first and second angles vary as the first and second image capturing devices are repositioned;

wherein the part is pretreated with a nital etchant solution, a mixture of alcohol and nitric acid; and wherein the computer is configured to compare the first and second sets of images of the part with the image of the second part devoid of flaws to determine if the part has defects.

2. The system of claim 1, wherein the part is a gear.

3. The system of claim 1, wherein the first image capturing device is a camera.

4. The system of claim 1, further comprising:
a lighting system operably associated with the computer, the lighting system being configured to illuminate the part.

5. The system of claim 1, further comprising:
a visual display operably associated with the computer, the visual display being configured to display the first set of images.

6. The system of claim 1, wherein the inspection system is a mobile device.

7. The system of claim 6, wherein the inspection system is a smartphone.

8. A method, comprising:
treating a part with a nital etchant solution;
capturing a first set of images of an outer surface of the part with a first image capturing device from a first angle;
selecting one of a plurality of different locations from which to capture a second set of images using a second image capturing device;
capturing the second set of images of the part with the second image capturing device from a second angle, the second angle being different from the first angle;
relaying the first and second sets of images to a computer;
identifying part flaws with an algorithm associated with the computer;

comparing the first and second sets of images with a second image of a second part devoid of defects; and
displaying the first and second sets of images on a display operably associated with the computer.

9. The method of claim 8, further comprising:
capturing a background image; and
suppressing the background image from the first set of images.

10. The method of claim 8, wherein the part is a gear.

11. The method of claim 10, further comprising:
detecting an edge of the gear from the first set of images.

12. The method of claim 11, further comprising:
correcting an angle orientation of the first set of images.

13. The method of claim 8, further comprising:
storing any flaws in the part in an image archive.

14. The method of claim 8, further comprising:
displaying the first set of images on a display operably associated with the computer.

15. The method of claim 8, further comprising:
Illuminating a gear with a lighting system.

16. The method of claim 8, wherein the computer is portable.

17. A method, comprising:
treating a gear with a nital etchant solution;
capturing a first set of images of an outer surface of the gear with a first image capturing device from a first angle;
selecting one of a plurality of different locations from which to capture a second set of images using a second image capturing device;
capturing the second set of images of the part with the second image capturing device from a second angle, the second angle being different from the first angle;
relaying the first and second sets of images to a computer;
identifying gear flaws with an algorithm associated with the computer by comparing the first and second sets of images with a second image of a second part devoid of defects; and
displaying the first and second sets of images on a display operably associated with the computer.

18. The method of claim 17, wherein the identifying a gear defect is achieved by identifying discolorations on the outer surface of the gear caused by the nital etchant solution.

* * * * *